United States Patent [19]
Theill et al.

[11] Patent Number: 5,859,197
[45] Date of Patent: Jan. 12, 1999

[54] NEUROGENE

[75] Inventors: Lars E. Theill, Malibu; Gregory S. Naeve, Newbury Park, both of Calif.; Yoav Citri, deceased, late of Tel-Aviv, Israel, by Reuven Greenbaum, executor

[73] Assignees: Amgen Inc., Thousand Oaks, Calif.; Yeda Research & Development Co, Ltd., Rehovot, Israel

[21] Appl. No.: 948,155

[22] Filed: Oct. 9, 1997

Related U.S. Application Data

[62] Division of Ser. No. 694,579, Aug. 9, 1996.

[51] Int. Cl.$^6$ .............................. C07K 1/00; C07K 14/00; C07K 17/00
[52] U.S. Cl. ....................... 530/350; 530/300; 530/827; 530/839; 530/855; 514/2
[58] Field of Search .................................... 530/350, 300, 530/827, 839, 855; 514/2

[56] References Cited

PUBLICATIONS

Jenner, *Neurology*, Suppl. 3: S6–S12 (1995).
Adams and Victor, eds. *Principles of Neurology*, Chapter 42: Degenerative Diseases of the Nervous System, McGraw Hill, NY (1993).
Fallon and Laughlin, *Neurotrophic Factors*, Academic Press, San Diego, CA (1993).
MacDonald and Hendrikson, *Cell*, 73: 421–424 (1993).
Lin et al., *Science*, 260: 1130–1132 (1993).
Yan et al., *Nature*, 373: 341–344 (1995).
Nedivi et al., *Nature*, 363: 718–722 (1993).
Nedivi et al., *Proc. Natl. Acad. Sci. USA*, 93: 2048–2052 (1996).
Isackson, *Current Opinions in Neurobiology*, 5: 50–357 (1995).
Humpel et al., *Science*, 269: 552–554 (1995).
Chomczynski et al., *Anal. Biochem.*, 162: 156–159 (1987).
Gubler et al., *Gene*, 25: 263–269 (1983).
Sive et al., *Nucleic Acids Res.*, 16: 10937 (1988).
Short et al., *Nucleic Acids Res.*, 16: 7583–7600 (1988).
Pearson et al., *Proc. Natl. Acad. Sci. USA*, 85: 2444–2448 (1988).
Simonet et al., *J. Biol. Chem.*, 11: 8221–8229 (1993).
Borchelt et al., *Glycolbiol.*, 3: 319–329 (1993).
Tsui et al., *Journal of Neuroscience*, 16(8): 2463–2478 (1996).
Naeve et al *PNAS* (1997) 94 pp. 2648–2653.
Grunwald et al *Visual Science* (1988) 29 p. 442.

*Primary Examiner*—Paula K. Hutzell
*Assistant Examiner*—Heather A. Bakalyar
*Attorney, Agent, or Firm*—Nancy A. Oleski; Ron K. Levy; Steven M. Odre

[57] ABSTRACT

Disclosed are DNA and amino acid sequences for a novel polypeptide termed Neuritin which is expressed primarily in selected regions of the brain.

5 Claims, 10 Drawing Sheets

FIG.1A

```
actctct                                                            7
cgtctctcttctgtctcctcgctccctctctcctcctcccctctgccttcccagt           67
gcataagtctctgtcgctcccggaacttgttggcaatgcctattttcagctttccccc      127
gcgttctctaaactaactatttaaaggtctgcggtcgcaaatggtttgactaaacgtagg    187
atgggacttaagttgaacggcagatatattcactgatcctcgcggtgcaaatagcttac     247
ctggtgcaggccgtgagagcagcaggcaagtgcgatgcagtctttaaggcttttcagac     307
tgtttgctcaagctggtggtgacatgccaactacccgcaggcctggacgacaagacg       367
aacatcaagaccgtgtgcacatactggaggatttccacagctgcacggtcacagctctt     427
acggattgccaggaaggggcgaaagatatgtgggataaactgagaaaagaatcgaaaaac    487
```

FIG. 1B

```
ctcaatatccaaggcagcttattcgaactctgcgcagcggcaacggggcggcgggtcc      547 ctgctcccggcgctttccgtgctcctgtgtctctcggcagctttagcgacctgcctt       607 tccttctgacttctgagcacggggccggtcccccctccgctcaccaccacactcact      667
ccatgctcccgaaatcgagaggaagagccattcgttctctcaaggacgttgtgattctct    727
gtgatattgaaaaacactcatatggattgtgtgggaaatccgtttctctctcttttttttt   787
ttaattttttttattttggttgagtcctgtgttttagttgccaaatgttaccgatcag      847
tgagcaaagcaagcacagccaaatcgacctcacctttttaattttgttttttacttacttattta 907
aagaaaacggcaaactgcaccccattttttaattttgttttttaattttacttactattta   967
tttatttatttttggcaaaagaaaaatctcaggaatggccctgggccacctactatattaat  1027
catgttgataacatgaaaaatgatggctcctctaatgagaaagcgaggagagaag         1087
gccaggggaatgagctcaagagtgatgccacagtgcccacgtggggaataatcgctcttcttc 1147
cacagtacccttgttttgatcattccacagcacattctcctccagaaacgcgaaaaaaca    1207
caagcgtgtgggttctgcattttttaaggatataagagagagaaagaggttgggtatagtagg 1267
acaggttgtcagagagatgctgctatggtcacgaggggccggtttcacctgctattgtc     1327
gtcgcctcctcagttccactgcttccactgcctttatgtccctctccctcttgttttagctgttac 1387
acatacagtaatacctgaatatccaacggtatagttcacaaggggtaatcaatgttaaa     1447
tctaaaatagaattttaaaaaaaagatttgacataaaagagccttgatttaaaaaaa       1507
aagagagatgtaatttaaaaagttttattataaattaaattcagcaaaaatttgctaca     1567
aagtatagagaagtataaataaagtttatgttttga                             1604
```

FIG.2

```
atgggacttaagttgaacggcagatatattcactgatcctcgcggtgcaaatagcgtat       60
ctggtgcaggccgtgagagcagcgggcaagtgcgatgcggtcttcaaggcttttcggac      120
tgtttgctcaagctgggcgacagcatggccaactacccgcaggcctgacgacaagacg      180
aacatcaagaccgtgtgcacatactgggaggatttccacagctgcacggtcacagccctt    240
acggattgccaggaaggggcgaaagatatgtgggataaactgagaaaagaatccaaaaac    300
ctcaacatccaaggcagcttattcgaactctgcggcagcggcaacggggcggcggggtcc    360
ctgctcccggcgttcccggtgctcctgtctctctcggcagctttagcgacctggctt       420
tccttctgagcacgg                                                   435
```

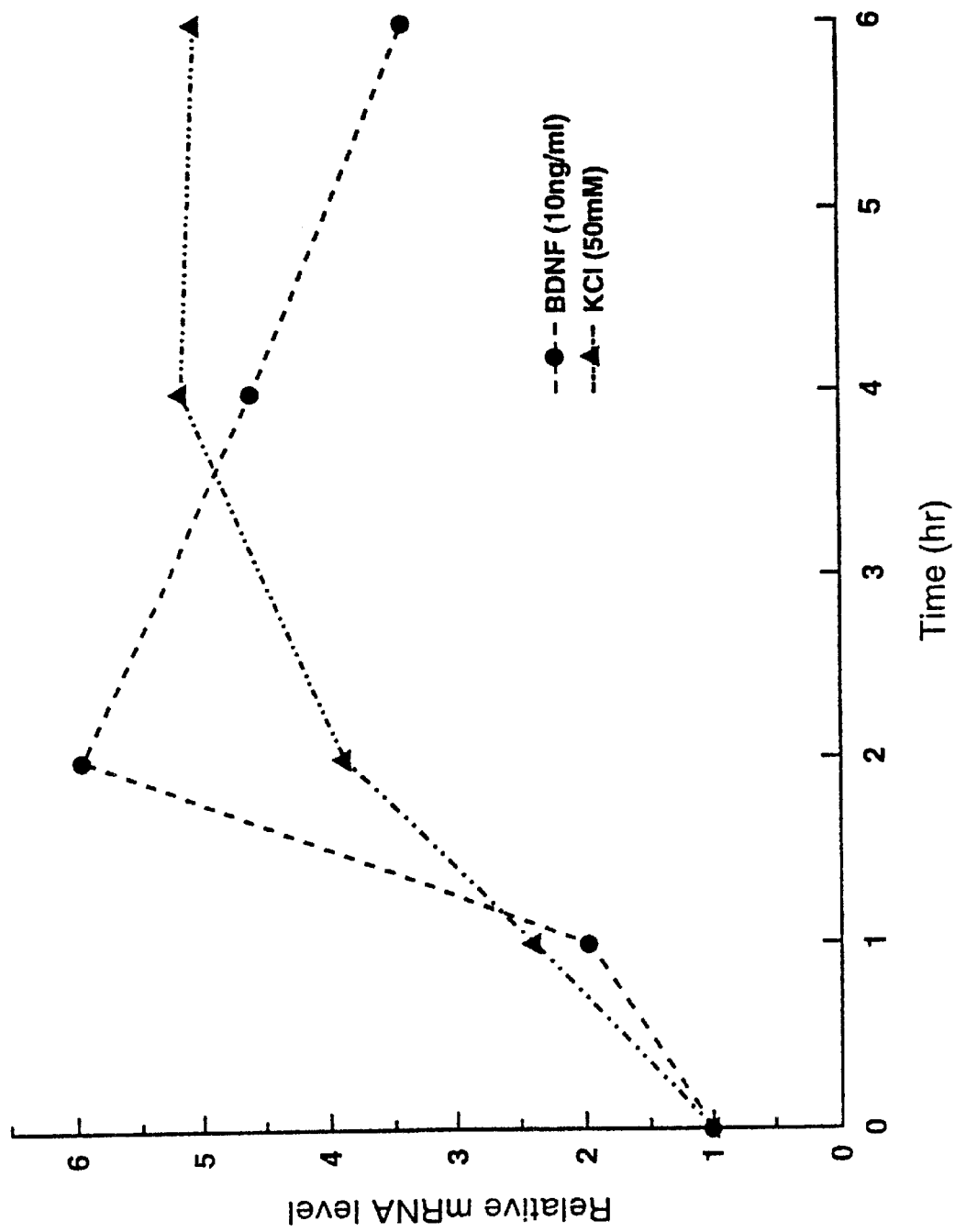

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1604 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ACTCTCTCGC TCTCTTTCTG TCTCTTCCTC GCTCCCTCTC TTTCTCTCCT CCCTCTGCCT      60
TCCCAGTGCA TAAAGTCTCT GTCGCTCCCG GAACTTGTTG GCAATGCCTA TTTTCAGCT      120
TTCCCCCGCG TTCTCTAAAC TAACTATTTA AAGGTCTGCG GTCGCAAATG GTTTGACTAA     180
ACGTAGGATG GGACTTAAGT TGAACGGCAG ATATATTTCA CTGATCCTCG CGGTGCAAAT     240
AGCTTACCTG GTGCAGGCCG TGAGAGCAGC AGGCAAGTGC GATGCAGTCT TTAAGGGCTT     300
TTCAGACTGT TTGCTCAAGC TGGGTGACAG CATGGCCAAC TACCCGCAGG GCCTGGACGA     360
CAAGACGAAC ATCAAGACCG TGTGCACATA CTGGGAGGAT TTCCACAGCT GCACGGTCAC     420
AGCTCTTACG GATTGCCAGG AAGGGGCGAA AGATATGTGG GATAAACTGA GAAAGAATC      480
GAAAAACCTC AATATCCAAG GCAGCTTATT CGAACTCTGC GGCAGCGGCA ACGGGGCGGC     540
GGGGTCCCTG CTCCGGCGC TTTCCGTGCT CCTGGTGTCT CTCTCGGCAG CTTTAGCGAC      600
CTGGCTTTCC TTCTGACTTC TGAGCACGGG GCCGGGTCCC CCCTCCGCTC ACCCACCCAC     660
ACTCACTCCA TGCTCCCGGA AATCGAGAGG AAGAGCCATT CGTTCTCTAA GGACGTTGTG     720
ATTCTCTGTG ATATTGAAAA CACTCATATG GGATTGTGGG AAATCCTGTT TCTCTCTTTT     780
TTTTTTTTA ATTTTTTTTT ATTTTGGTTG AGTCCTTGTG TTTTAGTTGC CAAATGTTAC      840
CGATCAGTGA GCAAAGCAAG CACAGCCAAA ATCGGACCTC ACCTTAAGTC CGTCTTCACA     900
CAAAATAAG AAAACGGCAA ACTCACCCCC ATTTTAATT TTGTTTTAA TTTTACTTAC        960
TTATTTATTT ATTTATTTT TGGCAAAAGA ATCTCAGGAA TGGCCCTGGG CCACCTACTA     1020
TATTAATCAT GTTGATAACA TGAAAAATGA TGGGCTCCTC CTAATGAGAA AGCGAGGAGA   1080
GGAGAAGGCC AGGGGAATGA GCTCAAGAGT GATGCCCACG TGGGAATAAT CGCTCACGTC   1140
TTTCTTCCAC AGTACCTTGT TTTGATCATT TCCACAGCAC ATTTCTCCTC CAGAAACGCG   1200
AAAAACACAA GCGTGTGGGT TCTGCATTTT TAAGGATAAG AGAGAGAAAG AGGTTGGGTA   1260
TAGTAGGACA GGTTGTCAGA AGAGATGCTG CTATGGTCAC GAGGGGCCGG TTTCACCTGC   1320
TATTGTCGTC GCCTCCTTCA GTTCCACTGC CTTTATGTCC CCTCCTCTCT CTTGTTTTAG   1380
CTGTTACACA TACAGTAATA CCTGAATATC CAACGGTATA GTTCACAAGG GGGTAATCAA   1440
TGTTAAATCT AAAATAGAAT TTAAAAAAAA AAGATTTTGA CATAAAGAG CCTTGATTTT    1500
AAAAAAAAG AGAGAGATGT AATTTAAAAA GTTATTATA AATTAAATTC AGCAAAATT      1560
TGCTACAAAG TATAGAGAAG TATAAAATAA AAGTTATTGT TTGA                    1604
```

( 2 ) INFORMATION FOR SEQ ID NO:2:

( i ) SEQUENCE CHARACTERISTICS:
        ( A ) LENGTH: 435 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ATGGACTTA  AGTTGAACGG  CAGATATATT  TCACTGATCC  TCGCGGTGCA  AATAGCGTAT     60
CTGGTGCAGG  CCGTGAGAGC  AGCGGGCAAG  TGCGATGCGG  TCTTCAAGGG  CTTTTCGGAC    120
TGTTTGCTCA  AGCTGGGCGA  CAGCATGGCC  AACTACCCGC  AGGGCCTGGA  CGACAAGACG    180
AACATCAAGA  CCGTGTGCAC  ATACTGGGAG  GATTTCCACA  GCTGCACGGT  CACAGCCCTT    240
ACGGATTGCC  AGGAAGGGGC  GAAAGATATG  TGGGATAAAC  TGAGAAAAGA  ATCCAAAAAC    300
CTCAACATCC  AAGGCAGCTT  ATTCGAACTC  TGCGGCAGCG  GCAACGGGGC  GGCGGGGTCC    360
CTGCTCCCGG  CGTTCCCGGT  GCTCCTGGTG  TCTCTCTCGG  CAGCTTTAGC  GACCTGGCTT    420
TCCTTCTGAG  CACGG                                                        435
```

( 2 ) INFORMATION FOR SEQ ID NO:3:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met  Gly  Leu  Lys  Leu  Asn  Gly  Arg  Tyr  Ile  Ser  Leu  Ile  Leu  Ala  Val
 1                  5                        10                       15
Gln  Ile  Ala  Tyr  Leu  Val  Gln  Ala  Val  Arg  Ala  Ala  Gly  Lys  Cys  Asp
               20                       25                       30
Ala  Val  Phe  Lys  Gly  Phe  Ser  Asp  Cys  Leu  Leu  Lys  Leu  Gly  Asp  Ser
          35                       40                       45
Met  Ala  Asn  Tyr  Pro  Gln  Gly  Leu  Asp  Asp  Lys  Thr  Asn  Ile  Lys  Thr
     50                       55                       60
Val  Cys  Thr  Tyr  Trp  Glu  Asp  Phe  His  Ser  Cys  Thr  Val  Thr  Ala  Leu
65                       70                       75                       80
Thr  Asp  Cys  Gln  Glu  Gly  Ala  Lys  Asp  Met  Trp  Asp  Lys  Leu  Arg  Lys
                    85                       90                       95
Glu  Ser  Lys  Asn  Leu  Asn  Ile  Gln  Gly  Ser  Leu  Phe  Glu  Leu  Cys  Gly
               100                      105                      110
Ser  Gly  Asn  Gly  Ala  Ala  Gly  Ser  Leu  Leu  Pro  Ala  Leu  Ser  Val  Leu
          115                      120                      125
Leu  Val  Ser  Leu  Ser  Ala  Ala  Leu  Ala  Thr  Trp  Leu  Ser  Phe
     130                      135                      140
```

( 2 ) INFORMATION FOR SEQ ID NO:4:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Gly  Leu  Lys  Leu  Asn  Gly  Arg  Tyr  Ile  Ser  Leu  Ile  Leu  Ala  Val
 1              5                        10                            15

Gln  Ile  Ala  Tyr  Leu  Val  Gln  Ala  Val  Arg  Ala  Ala  Gly  Lys  Cys  Asp
               20                       25                  30

Ala  Val  Phe  Lys  Gly  Phe  Ser  Asp  Cys  Leu  Leu  Lys  Leu  Gly  Asp  Ser
               35                       40                  45

Met  Ala  Asn  Tyr  Pro  Gln  Gly  Leu  Asp  Asp  Lys  Thr  Asn  Ile  Lys  Thr
     50                       55                       60

Val  Cys  Thr  Tyr  Trp  Glu  Asp  Phe  His  Ser  Cys  Thr  Val  Thr  Ala  Leu
 65                      70                       75                            80

Thr  Asp  Cys  Gln  Glu  Gly  Ala  Lys  Asp  Met  Trp  Asp  Lys  Leu  Arg  Lys
                    85                       90                            95

Glu  Ser  Lys  Asn  Leu  Asn  Ile  Gln  Gly  Ser  Leu  Phe  Glu  Leu  Cys  Gly
                    100                      105                 110

Ser  Gly  Asn  Gly  Ala  Ala  Gly  Ser  Leu  Leu  Pro  Ala  Phe  Pro  Val  Leu
               115                      120                 125

Leu  Val  Ser  Leu  Ser  Ala  Ala  Leu  Ala  Thr  Trp  Leu  Ser  Phe
     130                      135                      140
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:5:

CTAGTCTAGA ACCATGGGAC TTAAG    25

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:6:

GGTATAGTCG ACCCGTGCTC AGAA    24

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asp  Cys  Gln  Glu  Gly  Ala  Lys  Asp  Met  Trp  Asp  Lys  Leu  Arg  Lys
 1              5                        10                            15
```

( 2 ) INFORMATION FOR SEQ ID NO:8:

( i ) SEQUENCE CHARACTERISTICS:

```
            ( A ) LENGTH: 6 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:8:

Leu  Val  Pro  Arg  Gly  Ser
     1                     5

( 2 ) INFORMATION FOR SEQ ID NO:9:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:9:

Gln  Pro  Glu  Leu  Ala  Pro  Glu  Asp  Pro  Glu  Asp  Val  Glu
     1                     5                         1 0

( 2 ) INFORMATION FOR SEQ ID NO:10:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "SYNTHETIC DNA"

( x i ) SEQUENCE DESCRIPTION: SEQ ID NO:10:

CTAGTCTAGA  ACCATGGGAC  TTAAG                                              2 5

( 2 ) INFORMATION FOR SEQ ID NO:11:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "SYNTHETIC DNA"

( x i ) SEQUENCE DESCRIPTION: SEQ ID NO:11:

GGTATACTCG  AGCCCGTTGC  CGCT                                               2 4
```

NEUROGENE

This application is a division of application Ser. No. 08/694,579, filed Aug. 9, 1996, which is hereby incorporated by reference

BACKGROUND

1. Field of the Invention

This invention relates to novel DNA sequences encoding a polypeptide termed Neuritin, which is expressed primarily in certain brain tissues in response to certain stimuli.

2. Related Art

A number of neurological disorders and diseases are caused at least in part by degeneration or death of particular classes of neurons. For example, Parkinson's disease is characterized by slowing of voluntary muscle movement, muscular rigidity, and tremor. Such symptoms are attributed at least in part to progressive degeneration of dopamine-producing neurons located in a specific region of the brain called the substantia nigra. Degeneration of these neurons ("dopaminergic neurons") results in a decrease of dopamine levels in an adjacent region of the brain called the striatum. The striatum contains neurons expressing receptors for dopamine; these neurons are involved in the control of motor activity. The cause of the degeneration of dopaminergic neurons is unknown, but has been attributed to free radicals, excess iron content, environmental toxins, excitatory amino acid neurotoxicity, and possibly a deficiency of certain neurotrophic factors (Jenner, *Neurology, Suppl.* 3:S6–S12 [1995]; Adams and Victor, eds. *Principles of Neurology*, Chapter 42: Degenerative Diseases of the Nervous System, McGraw Hill, N.Y. [1993]).

Diseases such as amyotrophic lateral sclerosis (ALS), progressive muscular atrophy, and hereditary motor and sensory neuropathy (Charcot-Marie-Tooth disease) all result at least in part from a decay of motor neurons which are located in the ventral horn of the spinal cord.

The hippocampus, a well defined structure that is part of the cerebral cortex of the brain, is important in the formation of long term memory. Destruction of the hippocampus, for example by ischemia, can result in an inability to form new memories. Degeneration of pyramidal CA1 neurons, which are located in the CA1 region of the hippocampus, is one characteristic of Alzheimer's disease. These same neurons are selectively vulnerable to ischemic and anoxic damage which occur in conditions such as stroke and head trauma. In addition, the CA1 pyramidal hippocampal neurons as well as pyramidal neurons located in the CA3 region of the hippocampus, are selectively injured in epilepsy.

The striatum is the innervation region of the nerve terminals of dopaminergic-containing neurons from the substantia nigra. The majority of striatal neurons utilize GABA (4-aminobutyric acid) as their neurotransmitter. The striatum is the major target of the progressive neurodegeneration that occurs in Huntington's disease, in which the major neuron loss is that of the striatal GABA-utilizing neurons.

The serotonin-containing neurons are located in groups clustered around the midline of the hindbrain. These neurons are involved in the control of body temperature, mood, and sleep. Disorders of the serotonin-containing neuron system include, for example, depression, other mood disorders, and sleep disturbances.

Photoreceptor cells are a specialized subset of retina neurons, and are responsible for vision. Injury and/or death of photoreceptor cells can lead to blindness. Degeneration of the retina, such as by retinitis pigmentosa, age-related macular degeneration, and stationary night blindness, are all characterized by the progressive atrophy and loss of function of photoreceptor outer segments which are specialized structures containing the visual pigments that transform a light stimulus into electrical activity.

While there are some therapies available to treat the symptoms and decrease the severity of such diseases (e.g., L-dopa to treat Parkinson's disease), there currently exists no effective treatment to prevent or reduce the degeneration of most of the above mentioned classes of affected neurons, or to promote their repair.

Recently, several naturally occurring proteinaceous molecules have been identified based on their trophic activity on various neurons. These molecules are termed "neurotrophic factors". Neurotrophic factors are endogenous, soluble proteins that can regulate survival, growth, and/or morphological plasticity of neurons (see Fallon and Laughlin, *Neurotrophic Factors*, Academic Press, San Diego, Calif. [1993]).

The known neurotrophic factors belong to several different protein superfamilies of polypeptide growth factors based on their amino acid sequence homology and/or their three-dimensional structure (MacDonald and Hendrikson, *Cell*, 73:421–424 [1993]). One family of neurotrophic factors is the neurotrophin family. This family currently consists of NGF (nerve growth factor), BDNF (brain derived neurotrophic factor), NT-3 (neurotrophin-3), NT-4 (neurotrophin-4), and NT-6 (neurotrophin-6).

CNTF (ciliary neurotrophic factor) and LIF (leukemia inhibitory factor) are cytokine polypeptides that have neurotrophic activity. By virtue of their structural features and receptor components, these polypeptides are related to a family of hematopoietic cytokines that includes IL-6 (interleukin-6), IL-11 (interleukin-11), G-CSF (granulocyte-colony stimulating factor), and oncostatin-M.

GDNF (glial derived neurotrophic factor) is a neurotrophic factor that belongs to the TGF-beta (transforming growth factor beta) superfamily. GDNF displays potent survival and differentiation-promoting actions for dopaminergic and motor neurons (Lin et al., *Science*, 260:1130–1132 [1993]; Yan et al., *Nature*, 373:341–344 [1995]).

While these neurotrophic factors are known to increase growth and/or survival of neurons, there is less known about the molecules that work in conjunction with these factors. One manner in which additional neurotrophins and related molecules may be identified is to administer to an animal one or more compounds known to have an effect on the nervous system, and to then analyze tissues for the induction of genes involved in neural responses to the compounds. For example, one can screen for genes that are induced in certain tissues of the nervous system, such as the hippocampal region of the brain. This technique was used by Nedivi et al (*Nature*, 363:718–722 [1993]; Nedivi et al., *Proc. Natl. Acad. Sci USA*, 93:2048–2053 [1996]) to identify novel genes that are induced in the dentate gyrus portion of the hippocampus in response to administration of a neurotransmitter analog of glutamate called kainate (kainic acid).

Expression of many neurotrophic factors such as NGF, BDNF, NT3, GDNF, bFGF, IGF-1 and TGF-beta are regulated by afferent neuronal activity and/or by neuronal injury. Strong induction of some of these genes can be observed in the hippocampus dentate gyrus in response to the glutamate analog kainate (Isackson, *Current Opinions in Neurobiology* 5:50–357 [1995]). Kainate treatment appears to increase the release of novel compounds from the hippocampus of alert rats, and this activity appears to be different from the actions of known neurotrophic factors (Humpel, et al., *Science*, 269:552–554 [1995]).

In view of the fact that many nervous system disorders and diseases have no known cure, there is a need in the art to identify novel compounds for treating neurological conditions and diseases such as Parkinson's disease, amyotrophic lateral sclerosis (ALS), Alzheimer's disease, stroke, and various degenerative disorders that affect vision.

Accordingly, it is an object of the present invention to provide novel compounds that may be useful in promoting neuron regeneration and restoring neural functions.

It is a further object of the invention to provide a method of treating certain neurological diseases.

These and other objects will be apparent to one of ordinary skill in the art from the present disclosure.

SUMMARY OF THE INVENTION

In one embodiment, the present invention provides a nucleic acid molecule encoding a polypeptide selected from the group consisting of:
 (a) the nucleic acid molecule of SEQ ID NO:1;
 (b) the nucleic acid molecule of SEQ ID NO:2;
 (c) a nucleic acid molecule encoding the polypeptide of SEQ ID NO:3;
 (d) a nucleic acid molecule encoding the polypeptide of SEQ ID NO:4;
 (e) a nucleic acid molecule that encodes a polypeptide that is at least 70 percent identical to the polypeptide of SEQ ID NO:3 or SEQ ID NO:4; and
 (f) a nucleic acid molecule that is the complement of any of (a)–(e) above.

In another embodiment, the present invention provides vectors comprising the nucleic acid molecules set forth above.

In yet another embodiment, the present invention provides host cells comprising these vectors.

In still a further embodiment, the present invention provides a process for producing a Neuritin polypeptide comprising the steps of:
 (a) expressing a polypeptide encoded by the nucleic acid of claim 1 in a suitable host; and
 (b) isolating the polypeptide. Optionally, the Neuritin polypeptide is SEQ ID NO:3 or SEQ ID NO:4.

In yet another embodiment, the present invention provides a Neuritin polypeptide selected from the group consisting of:
 (a) the polypeptide of SEQ ID NO:3;
 (b) the polypeptide of SEQ ID NO:4; and
 (c) a polypeptide that is at least 70 percent homologous with the polypeptide of (a) or (b). Optionally, the Neuritin polypeptide may be a biologically active fragment of Neuritin, such as amino acids 25–115, 25–143, amino acids 1–115, or the like.

BRIEF DESCRIPTION OF THE DRAWINGS

FIG. 1 depicts a cDNA sequence of rat Neuritin (SEQ ID NO:1).

FIG. 2 depicts a cDNA sequence of human Neuritin (SEQ ID NO:2).

FIG. 3 depicts the full length translated amino acid sequence for rat Neuritin (SEQ ID NO:3).

FIG. 4 depicts the full length translated amino acid sequence of human Neuritin (SEQ ID NO:4).

FIG. 5A is a Northern blot of various rat tissues probed with a Neuritin probe. Abbreviations are h (heart); br (brain); sp (spleen); lu (lung); li (liver); m (muscle); k (kidney); t (testis).

FIG. 6A shows a Northern blot of rat hippocampal and cortical neurons treated with BDNF, NT-3, FGF, AMPA, NMDA, or KCl. Controls "0" received no treatment.

FIG. 7 is a graph of the time course induction of Neuritin mRNA levels in rat E-18 hippocampal neurons in response to treatment with either BDNF or KCl.

FIG. 8A depicts a Western blot of CHO cells transfected with either control plasmid ("parental") or plasmid containing the gene encoding full length human Neuritin (cell line termed "CHO 15.4"). "PI-PLC" refers to phosphinositol-phospholipase C, and "+" and "−" refer to the presence or absence of PI-PLC.

DETAILED DESCRIPTION OF THE INVENTION

Figure 5A:
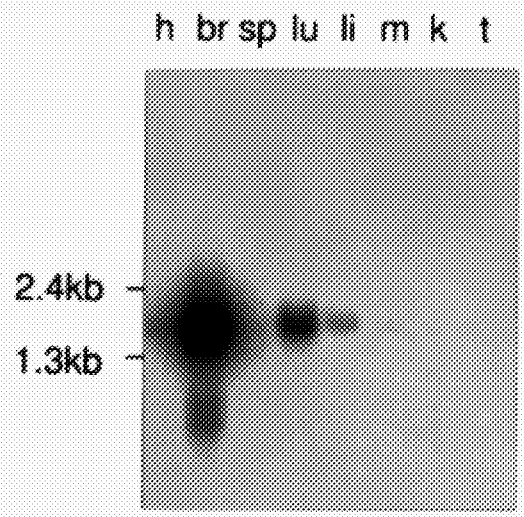
FIGS. 5A and B depict two Northern blots.

As used herein, the term "Neuritin" when used to describe a nucleic acid molecule refers to a nucleic acid molecule or fragment thereof that (a) has the nucleotide sequence as set forth in SEQ ID NO:1 or SEQ ID NO:2; (b) has a nucleic acid sequence encoding a polypeptide that is at least 70 percent identical, but may be at least 80 percent or 90 percent identical, to the polypeptide encoded by any of SEQ ID NOS:1 or 2; (c) is a naturally occurring allelic variant of (a) or (b); (d) is a nucleic acid variant of (a)–(c) produced as provided for herein; and/or (e) is complementary to (a)–(d).

Percent sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a predetermined portion of one or both sequences). The programs provide a "default" opening penalty and a "default" gap penalty, and a scoring matrix such as PAM 250 (a standard scoring matrix; see Dayhoff et al., in: *Atlas of Protein Sequence and Structure*, vol. 5, supp.3 [1978]) can be used in conjunction with the computer program. The percent identity can then be calculated as:

$$\frac{\text{Total number of indentical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions. Usually, the substitutions will be conservative so as to have little or no effect on the overall net charge, polarity, or hydrophobicity of the protein but optionally may increase the activity of Neuritin. Conservative substitutions are set forth in Table I below.

TABLE I

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The term "stringent conditions" refers to hybridization and washing under conditions that permit only binding of a nucleic acid molecule such as an oligonucleotide or cDNA molecule probe to highly homologous sequences. One stringent wash solution is 0.015M NaCl, 0.005M NaCitrate, and 0.1 percent SDS used at a temperature of 55° C.–65° C. Another stringent wash solution is 0.2×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35°–40° C., 17 base pair probes are washed at 45°–50° C., 20 base pair probes are washed at 52°–57° C., and 23 base pair probes are washed at 57°–63° C. The temperature can be increased 2°–3° C. where the background non-specific binding appears high. A second protocol utilizes tetramethylammonium chloride (TMAC) for washing oligonucleotide probes. One stringent washing solution is 3M TMAC, 50 mM Tris-HCl, pH 8.0, and 0.2 percent SDS. The washing temperature using this solution is a function of the length of the probe. For example, a 17 base pair probe is washed at about 45°–50° C.

The term "Neuritin protein" or "Neuritin polypeptide" as used herein refers to any protein or polypeptide having the properties described herein for Neuritin. The Neuritin polypeptide may or may not have an amino terminal methionine, depending on the manner in which it is prepared. By way of illustration, Neuritin protein or Neuritin polypeptide refers to (1) an amino acid sequence encoded by the nucleic acid molecule set forth in any of items (a)–(e) above and peptide or polypeptide fragments derived therefrom, (2) the amino acid sequence set forth in SEQ ID NOs:3 or 4, and/or (3) chemically modified derivatives as well as nucleic acid and or amino acid sequence variants thereof as provided for herein.

As used herein, the term "Neuritin fragment" refers to a peptide or polypeptide that is less than the full length amino acid sequence of naturally occurring Neuritin protein but has substantially the same biological activity as Neuritin polypeptide or Neuritin protein described above. Such a fragment may be truncated at the amino terminus, the carboxy terminus (such as the GPI anchoring domain which is about the last 27 amino acids of the Neuritin polypeptide), and/or internally, and may be chemically modified. Preferably, the Neuritin fragment will be one which retains at least all 6 cysteine residues. Such Neuritin fragments may be prepared with or without an amino terminal methionine.

Figure 3:
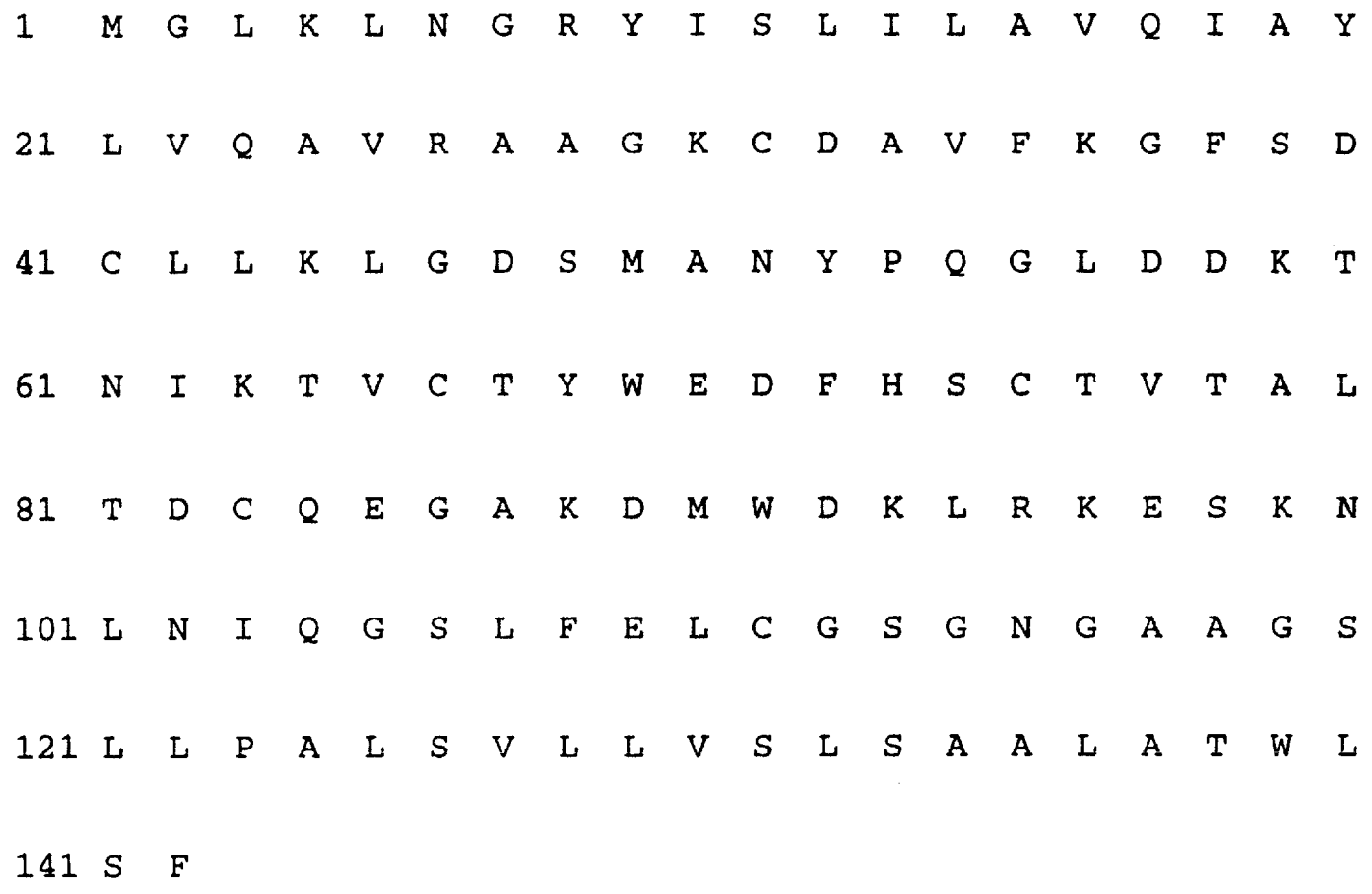

As used herein, the term "Neuritin derivative" or "Neuritin variant" refers to a Neuritin polypeptide or Neuritin protein that has 1) been chemically modified, as for example, by addition of polyethylene glycol or other compound, and/or 2) contains one or more nucleic acid or amino acid sequence substitutions, deletions, and/or insertions as compared to Neuritin set forth in FIGS. 3 or 4.

As used herein, the terms "biologically active polypeptide" and "biologically active fragment" refer to a peptide or polypeptide that has Neuritin activity, i.e., promotes neuritogenesis in hippocampal or cortical neuronal cultures.

As used herein, the terms "effective amount" and "therapeutically effective amount" refer to the amount of Neuritin necessary to support one or more biological activities of Neuritin as set forth above.

The Neuritin polypeptides that have use in practicing the present invention may be naturally occurring full length polypeptides, or truncated polypeptides or peptides (i.e, "fragments"). The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring Neuritin polypeptide (i.e., may contain one or more amino acid deletions, insertions, and/or substitutions as compared with naturally occurring Neuritin).

The full length Neuritin polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, N.Y. [1994]). A gene or cDNA encoding the Neuritin protein or fragment thereof may be obtained for example by screening a genomic or cDNA library, or by PCR amplification. Alternatively, a gene encoding the Neuritin polypeptide or fragment may be prepared by chemical synthesis using methods well known to the skilled artisan such as those described by Engels et al.(*Angew. Chem. Intl. Ed.*, 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the Neuritin polypeptide will be several hundred nucleotides in length. Nucleic acids larger than about 100 nucleotides can be synthesized as several fragments using these methods. The fragments can then be ligated together to form the full length Neuritin polypeptide. Usually, the DNA fragment encoding the amino terminus of the polypeptide will have an ATG, which encodes a methionine residue. This methionine may or may not be present on the mature form of the Neuritin polypeptide, depending on whether the polypeptide produced in the host cell is secreted from that cell.

In some cases, it may be desirable to prepare nucleic acid and/or amino acid variants of naturally occurring Neuritin. Nucleic acid variants (wherein one or more nucleotides are designed to differ from the wild-type or naturally occurring Neuritin) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce Neuritin. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on Neuritin, or those designed to delete an existing glycosylation and/or phosphorylation site(s) on Neuritin.

The Neuritin gene or cDNA can be inserted into an appropriate expression vector for expression in a host cell. The vector is selected to be functional in the particular host cell employed (i.e., the vector is compatible with the host cell machinery such that amplification of the Neuritin gene and/or expression of the gene can occur). The Neuritin polypeptide or fragment thereof may be amplified/expressed in prokaryotic, yeast, insect (baculovirus systems) and/or eukaryotic host cells. Selection of the host cell will depend at least in part on whether the Neuritin polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the Neuritin polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the Neuritin coding sequence that encodes polyHis (such as hexaHis) or another small immunogenic sequence. This tag will be expressed along with the protein, and can serve as an affinity tag for purification of the Neuritin polypeptide from the host cell. Optionally, the tag can subsequently be removed from the purified Neuritin polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native Neuritin 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the Neuritin 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the Neuritin polypeptide. If the vector of choice does not contain an origin of replication site, one may be chemically synthesized based on a known sequence, and ligated into the vector.

The transcription termination element is typically located 3' to the end of the Neuritin polypeptide coding sequence and serves to terminate transcription of the Neuritin polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the Neuritin polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for Neuritin to be secreted from the host cell, a signal sequence may be used to direct the Neuritin polypeptide out of the host cell where it is synthesized, and the. carboxy-terminal part of the protein may be deleted in order to prevent membrane anchoring. Typically, the signal sequence is positioned in the coding region of Neuritin nucleic acid sequence, or directly at the 5' end of the Neuritin coding region. Many signal sequences have been identified, and any of them that are functional in the selected host cell may be used in conjunction with the Neuritin gene. Therefore, the signal sequence may be homologous or heterologous to the Neuritin polypeptide, and may be homologous or heterologous to the Neuritin polypeptide. Additionally, the signal sequence may be chemically synthesized using methods set forth above. In most cases, secretion of the polypeptide from the host cell via the presence of a signal peptide will result in the removal of the amino terminal methionine from the polypeptide. To facilitate secretion, the C-terminal region of the Neuritin polypeptide may be removed. This C-terminal region is about 27 amino acids in length, and many of the amino acids are hydrophobic; further, there is a consensus cleavage signal sequence which is found in many glycosylphoshatidylinositol (GPI) anchored proteins in this region.

In many cases, transcription of the Neuritin polypeptide is increased by the presence of one or more introns on the vector; this is particularly true for eukaryotic host cells, especially mammalian host cells. The intron may be naturally occurring within the Neuritin nucleic acid sequence, especially where the Neuritin sequence used is a full length genomic sequence or a fragment thereof. Where the intron is not naturally occurring within the Neuritin DNA sequence (as for most cDNAs), the intron(s) may be obtained from another source. The position of the intron with respect to the 5' flanking sequence and the Neuritin coding sequence is important, as the intron must be transcribed to be effective. As such, where the Neuritin nucleic acid sequence is a cDNA sequence, the preferred position for the intron is 3' to the transcription start site, and 5' to the polyA transcription termination sequence. Preferably for Neuritin cDNAs, the intron will be located on one side or the other (i.e., 5' or 3') of the Neuritin coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible-for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII (Invitrogen Company, San Diego, Calif.), PBSII (Stratagene Company, Lajolla, Calif.), and PETL (BlueBacII; Invitrogen).

After the vector has been constructed and a Neuritin nucleic acid has been inserted into the proper site of the vector, the completed vector may be inserted into a suitable host cell for amplification and/or Neuritin polypeptide expression.

Host cells may be prokaryotic host cells (such as E. coli) or eukaryotic host cells (such as a yeast cell, an insect cell, or a vertebrate cell). The host cell, when cultured under appropriate conditions, can synthesize Neuritin protein which can subsequently be collected from the culture medium (if the host cell secretes it into the medium) or directly from the host cell producing it (if it is not secreted). After collection, the Neuritin protein can be purified using methods such as molecular sieve chromatography, affinity chromatography, and the like.

Selection of the host cell will depend in part on whether the Neuritin protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active Neuritin, the Neuritin may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of *biotechnology*. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8: 277–298 [1986]).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of Neuritin polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the Neuritin polypeptide has been designed to be secreted from the host cells, the majority of polypeptide will likely be found in the cell culture medium. Polypeptides prepared in typically no typically not possess an amino terminal methionine, as it is removed during secretion from the cell. If however, the Neuritin polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular Neuritin protein, the host cells are typically first disrupted mechanically or osmotically to release the cytoplasmic contents into a buffered solution. Neuritin polypeptide can then be isolated from this solution.

Purification of Neuritin polypeptide from solution can be accomplished using a variety of techniques. If the polypeptide has been synthesized such that it contains a tag such as Hexahistidine (Neuritin/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing Neuritin). For example, polyhistidine binds with great affinity and specificity to nickel, thus an affinity column of nickel (such as the Qiagen nickel columns) can be used for purification of Neuritin/polyHis. (See for example, Ausubel et al., eds., *Current Protocols in Molecular Biology*, Section 10.11.8, John Wiley & Sons, New York [1993]).

Where the Neuritin polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the Neuritin polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the Neuritin polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The Neuritin polypeptide in its now soluble form can then be analyzed using gel electrophoresis, immunoprecipitation or the like. If it is desired to isolate the Neuritin polypeptide, isolation may be accomplished using standard methods such as those set forth below and in Marston et al. (*Meth. Enz.*, 182:264–275 [1990]).

If Neuritin polypeptide inclusion bodies are not formed to a significant degree in the periplasm of the host cell, the Neuritin polypeptide will be found primarily in the supernatant after centrifugation of the cell homogenate, and the Neuritin polypeptide can be isolated from the supernatant using methods such as those set forth below.

In those situations where it is preferable to partially or completely isolate the Neuritin polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying Neuritin polypeptide using recombinant DNA techniques, the Neuritin polypeptides, fragments, and/or derivatives thereof may be prepared by chemical synthesis methods (such as solid phase peptide synthesis) using methods known in the art such as those set forth by Merrifield et al., (*J. Am. Chem. Soc.*, 85:2149 [1964]), Houghten et al. (*Proc Natl Acad. Sci. USA*, 82:5132 [1985]), and Stewart and Young (Solid Phase Peptide Synthesis, Pierce Chem Co, Rockford, Ill. [1984]). Such polypeptides may be synthesized with or without a methionine on the amino terminus. Chemically synthesized Neuritin polypeptides or fragments may be oxidized using methods set forth in these references to form disulfide bridges. The Neuritin polypeptides or fragments may be employed as biologically active or immunological substitutes for natural, purified Neuritin polypeptides in therapeutic and immunological processes.

Chemically modified Neuritin compositions (i.e., "derivatives") where the Neuritin polypeptide is linked to a polymer ("Neuritin-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Included within the scope of Neuritin-polymers is a mixture of polymers. Preferably, for therapeutic use of the end-product preparation, the polymer will be pharmaceutically acceptable. The water soluble polymer or mixture thereof may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. For the acylation reactions, the polymer (s) selected should have a single reactive ester group. For reductive alkylation, the polymer(s) selected should have a single reactive aldehyde group. The polymer may be of any molecular weight, and may be branched or unbranched.

Pegylation of Neuritin may be carried out by any of the pegylation reactions known in the art, as described for example in the following references: Focus on Growth Factors 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

Pegylation by acylation generally involves reacting an active ester derivative of polyethylene glycol (PEG) with an Neuritin protein. Any known or subsequently discovered reactive PEG molecule may be used to carry out the pegylation of Neuritin. A preferred activated PEG ester is PEG esterified to N-hydroxysuccinimide ("NHS"). As used herein, "acylation" is contemplated to include without limitation the following types of linkages between Neuritin and a water soluble polymer such as PEG: amide, carbamate, urethane, and the like, as described in *Bioconjugate Chem.* 5: 133–140 (1994). Reaction conditions may be selected from any of those known in the pegylation art or those subsequently developed, provided that conditions such as temperature, solvent, and pH that would inactivate the Neuritin species to be modified are avoided.

Pegylation by acylation usually results in a polypegylated Neuritin product, wherein the lysine εamino groups are pegylated via an acyl linking group. Preferably, the connecting linkage will be an amide. Also preferably, the resulting product will be at least about 95 percent mono, di- or tri-pegylated. However, some species with higher degrees of pegylation (up to the maximum number of lysine ε-amino acid groups of Neuritin plus one α-amino group at the amino terminus of Neuritin) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with a protein such as Neuritin in the presence of a reducing agent. Regardless of the degree of pegylation, the PEG groups are preferably attached to the protein via a —$CH_2$—NH— group. With particular reference to the —$CH_2$—group, this type of linkage is referred to herein as an "alkyl" linkage.

Derivatization via reductive alkylation to produce a monopegylated product exploits the differential reactivity of different types of primary amino groups (lysine versus the N-terminal) available for derivatization in Neuritin. Typically, the reaction is performed at a pH (see below) which allows one to take advantage of the $pK_a$ differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer occurs predominantly at the N-terminus of the protein without significant modification of other reactive groups such as the lysine side chain amino groups. The present invention provides for a substantially homogeneous preparation of Neuritin-monopolymer protein conjugate molecules (meaning Neuritin protein to which a polymer molecule has been attached substantially only (i.e., at least about 95%) in a single location on the Neuritin protein. More specifically, if polyethylene glycol is used, the present invention also provides for pegylated Neuritin protein lacking possibly antigenic linking groups, and having the polyethylene glycol molecule directly coupled to the Neuritin protein.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy—or aryloxy-polyethylene glycol.

In general, chemical derivatization may be performed under any suitable conditions used to react a biologically active substance with an activated polymer molecule. Methods for preparing pegylated Neuritin will generally comprise the steps of (a) reacting an Neuritin polypeptide with polyethylene glycol (such as a reactive ester or aldehyde derivative of PEG) under conditions whereby Neuritin becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Reductive alkylation to produce a substantially homogeneous population of mono-polymer/Neuritin protein conjugate molecule will generally comprise the steps of: (a) reacting a Neuritin protein with a reactive PEG molecule under reductive alkylation conditions, at a pH suitable to permit selective modification of the α-amino group at the amino terminus of said Neuritin protein; and (b) obtaining the reaction product(s).

For a substantially homogeneous population of monopolymer/Neuritin protein conjugate molecules, the reductive alkylation reaction conditions are those which permit the selective attachment of the water soluble polymer moiety to the N-terminus of Neuritin. Such reaction conditions generally provide for $pK_a$ differences between the lysine amino groups and the α-amino group at the N-terminus (the $PK_a$ being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2kDa to about 100kDa (the term "about" indicating ±1kDa). The preferred average molecular weight is about 5kDa to about 50kDa, particularly preferably about 12kDa to about 25kDa. The ratio of water-soluble polymer to Neuritin protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any Neuritin protein having an α-amino group at the amino terminus, and provide for a substantially homogenous preparation of monopolymer/Neuritin protein conjugate. The term "monopolymer/Neuritin protein conjugate" is used here to mean a composition comprised of a single polymer molecule attached to an Neuritin protein molecule. The monopolymer/Neuritin protein conjugate preferably will have a polymer molecule located at the N-terminus, but not on lysine amino side groups. The preparation will preferably be greater than 90% monopolymer/Neuritin protein conjugate, and more preferably greater than 95% monopolymer Neuritin protein conjugate, with the remainder of observable molecules being unreacted (i.e., protein lacking the polymer moiety). The examples below provide for a preparation which is at least about 90% monopolymer/ protein conjugate, and about 10% unreacted protein. The monopolymer/protein conjugate has biological activity.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borane, trimethylamine borane and pyridine borane. A particularly preferred reducing agent is sodium cyanoborohydride.

Other reaction parameters, such as solvent, reaction times, temperatures, etc., and means of purification of products, can be determined based on the published information relating to derivatization of proteins with water soluble polymers.

A mixture of polymer-Neuritin protein conjugate molecules may be prepared by acylation and/or alkylation methods, as described above, and one may select the proportion of monopolymer/ protein conjugate to include in the mixture. Thus, where desired, a mixture of various protein with various numbers of polymer molecules attached (i.e., di-, tri-, tetra-, etc.) may be prepared and combined with the monopolymer/Neuritin protein conjugate material prepared using the present methods.

Generally, conditions which may be alleviated or modulated by administration of the present polymer/Neuritin include those described herein for Neuritin molecules in general. However, the polymer/Neuritin molecules disclosed herein may have additional activities, enhanced or reduced activities, or other characteristics, as compared to the non-derivatized molecules.

Neuritin nucleic acid molecules, fragments, and/or derivatives that do not themselves encode polypeptides that are active in activity-assays may be useful as hybridization probes in diagnostic assays to test, either qualitatively or quantitatively, for the presence of Neuritin DNA or RNA in mammalian tissue or bodily fluid samples.

Neuritin polypeptide fragments and/or derivatives that are not themselves active in activity assays may be useful as modulators (e.g., inhibitors or stimulants) of the Neuritin receptors in vitro or in vivo, or to prepare antibodies to Neuritin polypeptides.

The Neuritin polypeptides and fragments thereof, whether or not chemically modified, may be employed alone, or in combination with other pharmaceutical compositions such as, for example, neurotrophic factors, cytokines, interferons, interleukins, growth factors, antibiotics, anti-inflammatories, neurotransmitter receptor agonists or antagonists and/or antibodies, in the treatment of neurological system disorders.

The Neuritin polypeptides and/or fragments thereof may be used to prepare antibodies generated by standard methods. Thus, antibodies that react with the Neuritin polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will be "humanized", i.e., prepared so as to prevent or minimize an immune reaction to the antibody when administered to a patient. The antibody fragment may be any fragment that is reactive with the Neuritin of the present invention, such as, $F_{ab}$, $F_{ab'}$, etc. Also provided by this invention are the hybridomas generated by presenting Neuritin or a fragment thereof as an antigen to a selected mammal, followed by fusing cells (e.g., spleen cells) of the animal with certain cancer cells to create immortalized cell lines by known techniques. The methods employed to generate such cell lines and antibodies directed against all or portions of a human Neuritin polypeptide of the present invention are also encompassed by this invention.

The antibodies may be used therapeutically, such as to inhibit binding of Neuritin to its receptor. The antibodies may further be used for in vivo and in vitro diagnostic purposes, such as in labeled form to detect the presence of the Neuritin in a body fluid.

Therapeutic Compositions and Administration

Therapeutic compositions for treating various neurological system disorders are within the scope of the present invention. Such compositions may comprise a therapeutically effective amount of a Neuritin polypeptide or fragment thereof (either of which may be chemically modified) in admixture with a pharmaceutically acceptable carrier. The carrier material may be water for injection, preferably supplemented with other materials common in solutions for administration to mammals. Typically, a Neuritin therapeutic compound will be administered in the form of a composition comprising purified protein (which may be chemically modified) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The Neuritin compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of Neuritin compositions useful for practicing the present invention may be prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The Neuritin composition to be used for in vivo administration must be sterile. This is readily accomplished by filtration through sterile filtration membranes. Where the Neuritin composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, Neuritin may be administered locally via implantation into the affected area of a membrane, sponge, or other appropriate material on to which Neuritin polypeptide has been absorbed.

Where an implantation device is used, the device may be implanted into any suitable tissue or organ, such as, for example, into a cerebral ventricle or into brain parenchyma, and delivery of Neuritin may be directly through the device via bolus or continuous administration, or via a catheter using continuous infusion.

Neuritin polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers*, 22: 547–556 [1983]), poly (2-hydroxyethyl-methacrylate) (Langer et al., *J. Biomed. Mater. Res.*, 15: 167–277 [1981] and Langer, *Chem. Tech.*, 12: 98–105 [1982]), ethylene vinyl acetate (Langer et al., supra) or poly-D(–)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA*, 82: 3688–3692 [1985]; Hwang et al., *Proc. Natl. Acad. Sci. USA*, 77: 4030–4034 [1980]; EP 52,322; EP 36,676; EP 88,046; EP 143,949).

In some cases, it may be desirable to use Neuritin compositions in an ex vivo manner, i.e., to treat cells or tissues that have been removed from the patient and are then subsequently implanted back into the patient.

In other cases, Neuritin may be delivered through implanting into patients certain cells that have been genetically engineered (using methods described above) to express and secrete Neuritin polypeptide. Such cells may be human cells, and may be derived from the patient's own tissue or from another source, either human or non-human. Optionally, the cells may be immortalized. The cells may be implanted into the brain, adrenal gland or into other body tissues or organs.

In certain situations, it may be desirable to use gene therapy methods for administration of Neuritin to patients suffering from certain neurological disorders. In these situations, genomic DNA, cDNA, and/or synthetic DNA encoding Neuritin or a fragment or variant thereof may be operably linked to a constitutive or inducible promoter that is active in the tissue into which the composition will be injected. This Neuritin DNA construct, either inserted into a vector, or alone without a vector, can be injected directly into brain or other tissue, either neuronal or non-neuronal.

Alternatively, a Neuritin DNA construct may be directly injected into muscle tissue where it can be taken up, into the cells and expressed in the cells, provided that the Neuritin DNA is operably linked to a promoter that is active in muscle tissue such as cytomegalovirus (CMV) promoter, Rous sarcoma virus (RSV) promoter, or muscle creatine kinase promoter. Typically, the DNA construct may include (in addition to the Neuritin DNA and a promoter), vector sequence obtained from vectors such as adenovirus vector, adeno-associated virus vector, a retroviral vector, and/or a herpes virus vector. The vector/DNA construct may be admixed with a pharmaceutically acceptable carrier(s) for injection.

An effective amount of the Neuritin composition(s) to be employed therapeutically will depend, for example, upon the therapeutic objectives such as the indication for which Neuritin is being used, the route of administration, and the condition of the patient. Accordingly, it will be necessary for the therapist to titer the dosage and modify the route of administration as required to obtain the optimal therapeutic effect. A typical daily dosage may range from about 0.1 μg/kg to up to 100 mg/kg or more, depending on the factors mentioned above. Typically, a clinician will administer the Neuritin composition until a dosage is reached that achieves the desired effect. The Neuritin composition may therefore be administered as a single dose, or as two or more doses (which may or may not contain the same amount of Neuritin) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing. Generally, the dosage will be between 0.01 μg/kg body weight (calculating the mass of the protein alone, without chemical modification) and 300 μg/kg (based on the same).

The Neuritin proteins, fragments and/or derivatives thereof may be utilized to treat diseases and disorders of the central or peripheral nervous system which may be associated with alterations in the pattern of Neuritin expression or which may benefit from exposure to Neuritin or anti-Neuritin antibodies.

Neuritin protein and/or fragments or derivatives thereof, may be used to treat patients in whom various cells of the central, autonomic, or peripheral nervous system have degenerated and/or have been damaged by congenital disease, trauma, mechanical damage, surgery, stroke, ischemia, infection, metabolic disease, nutritional deficiency, malignancy, and/or toxic agents. More specifically, Neuritin protein levels may be modulated (up or down regulated) for such indications as Alzheimer's, Parkinson's, amyotrophic lateral sclerosis, Charcot-Marie-Tooth syndrome, Huntington's disease, peripheral neuropathy induced by diabetes or other metabolic disorder, and/or dystrophies or degeneration of the neural retina such as retinitis pigmentosa, drug-induced retinopathies, stationary forms of night blindness, stationary forms of night blindness, progressive cone-rod degeneration, and the like.

In other embodiments of the present invention, Neuritin protein or peptide, or fragments or derivatives thereof, can be used in conjunction with surgical implantation of tissue in the treatment of diseases in which tissue implantation is indicated.

Deposit of DNA

*E. coli* cells containing the plasmid pCRScript SK+ into which the cDNA encoding full length human Neuritin (amino acids 1–142) has been inserted have been deposited with the ATCC (American Type Culture Collection, 12301 Parklawn Drive, Rockville, Md., USA) on Aug. 9, 1996 as accession number 98134.

The following examples are intended for illustration purposes only, and should not be construed as limiting the scope of the invention in any way.

EXAMPLES

Example I

Cloning of Neuritin cDNA

Male rats (Wistar) of about age 8–10 weeks (about 230–300 grams in weight) were injected intraperitoneal with about 8 mg/kg body weight of kainate (prepared in a stock solution of 5 mg/ml kainate in phosphate saline buffer [PBS]). About six hours later, the animals were sacrificed, and the dentate gyrus (DG) region of the brain was removed and stored in liquid $N_2$. DG tissue from about 100 animals was pooled, and RNA from this tissue was prepared by a modification of the guanidinium thiocyanate method ("GTC"; Chomczynski et al., *Anal. Biochem.*, 162:156 [1987]). After lysis of the tissue in GTC, 2 phenol extractions followed by and one chloroform extraction were performed, and the RNA was precipitated and resuspended in $H_{20}$. Poly (A)+ RNA was selected using oligo-(dT)-cellulose columns (Clontech, Palo Alto, Calif.). This RNA (and corresponding cDNA) is referred to herein as "activated DG" RNA or cDNA.

For subtraction analysis, library construction, and cDNA probing (all of which are described below), the RNA was treated with DNase (RNase free; Promega, Madison, Wis.) to eliminate any contaminating genomic DNA.

The same protocol set forth above was used to prepare poly(A)+ RNA from normal dentate gyrus tissue and total brain tissue of male rats of the same age that were not treated with kainate.

First strand cDNA was synthesized in two 50 ul reactions using activated-DG poly (A)+ RNA prepared as described above. Each reaction contained about 5 ug RNA in about 30 ul reverse transcriptase buffer (Gubler et al., *Gene*, 25:263–269 [1983]), about 1 ul RNase (4u/ul; Promega, Madison, Wis.), about 1ug oligo-(dT)-XbaI primer adapter (Promega, Madison, Wis.), about 30 uCi $^{32}$p dCTP (about 3,000 Ci/mmole, Amersham, Arlington Heights, Ill.) and about 400 u MLV cloned reverse transcriptase (BRL; Grand Island, N.Y.). After about 60 minutes at about 37° C., the RNA was hydrolyzed for about 20 minutes at about 68° C. by adding about 10 ul NaOH (1N), about 2 ul EDTA (0.5M) and $H_2O$ up to about 100 ul. The RNA was then placed on ice, and then neutralized with about 10 ul of 1M HCl. About 5 ug of transfer RNA was added, and the mixture was spun through a Sephadex G-50 spin-column. The recovery of cDNA was determined by comparing radioactivity in the column eluate to that in the sample originally applied to the column. The two cDNA samples were pooled, ethanol precipitated with $NH_4$Acetate, and resuspended to about 10 ng/ul in $H_2O$.

The cDNA was mixed with equal volume of total rat brain poly (A)+ RNA (1 ug/ul) previously coupled to biotin using two rounds of photobiotinylation (Clontech, Palo Alto, Calif.; see Sive et al., *Nucleic Acids Res.*, 16:10937 [1988]) and then ethanol precipitated with $NH_4$Acetate. After resuspension to about 100 ng/ul cDNA and about 10 ug/ul RNA in formamide buffer (40% formamide, 50 mM Hepes pH 7.6, 0.5M NaCl, 2 mM EDTA), the solution was placed into glass capillaries (25 μl each) that were sealed. The capillaries were incubated about 3 minutes at 68° C. and then for two days at 52° C. The capillaries were broken open and the contents of each was added to about 180 μl buffer (Hepes pH 7.6 50 mM, NaCl 0.5M, EDTA 2 mM). Streptavidin (Vector Labs, Burlingame, Calif.) was added at about 1 μg per μl of biotinylated RNA, and the mixtures were incubated about 10 minutes at room temperature. After incubation, two phenol/chloroform extractions (1 volume: 1 volume) and one chloroform extraction were conducted. The recovered aqueous phase typically contained 10–20% of the total cDNA used for subtraction cloning. This single stranded cDNA was ethanol precipitated and resuspended in about 16 μl of water.

About 1 ul dATP (10 mM) and about 4 μl 5× TdT buffer (Boehringer Manheim) were added to the cDNA. After about 3 minutes at 100° C. and cooling on ice, terminal deoxynucleotidyl transferase (17 μl, Boehringer, Manheim, Germany) was added and the mixture was incubated for about 2 hours at about 37° C. Two micrograms of oligo-(dT)-XbaI (Promega, Madison Wisc.) primer adapter were added, and the mixture was incubated about 5 minutes at 60° C. Second strand synthesis was conducted in about 50 ul total volume containing 90 mM Hepes buffer pH 6.6, MgCl 10 mM, all 4 deoxynucleotide triphosphates at a concentration of about 0.5 mM each, about 10 mM DTT, and 10 U Klenow (Boehringer Manheim sequencing grade). After about 6 hours at room temperature, another aliquot of enzyme was added, and the mixture was incubated for an additional three hours. The reaction was stopped with phenol and chloroform extractions, after which 5 ug transfer RNA was added, and the cDNA was ethanol precipitated with $NH_4$Acetate. The double stranded cDNA was resuspended in about 9.6 ul $H_2O$ and digested for 5 hours at 37° C. with 10 U of the restriction enzyme XbaI (Boehringer), after which it was loaded on to a thin 1% agarose gel and electrophoresed. A gel-slice containing cDNA molecules greater than about 550 base pairs ("bp") in size was excised, the cDNA was extracted using QIAEX (Qiagen Corp., Chatsworth, Calif.) and recovery (about 10% of the total subtracted cDNA) was determined by radioactive counting. This cDNA was ligated into lambda-ZAP (Stratagene, La Jolla, Calif.) vector arms that were previously digested with XbaI, and treated with Calf Intestinal Phosphatase (Boehringer Manheim). Ligations were conducted using about 1 ul phage arms and various concentrations of cDNA (3–20 ng). The ligations were packaged (Gigapack, Stratagene, La Jolla, Calif.) phage titer was determined. The library was plated at low density, individual plaques were picked separately, and plasmids in the vector pBluescript were excised from the phage following the manufacturer's protocol (see Short et al., *Nucleic Acids Res.* 16:7583–7600 [1988]). Plasmid DNA was then prepared from *E. coli* cells previously transformed with the pBluescript plasmids using standard minipreparation procedures (see Sambrook et al, *Molecular Cloning:* A Laboratory Manual, Cold Spring Harbor Laboratory Press, Cold Spring Harbor, N.Y. [1989]). About two to four ug of plasmid DNA obtained from the minipreparation were digested with XbaI and Southern blotted onto Hybond N+ filters (Amersham, Arlington Heights, Ill.) using standard procedures.

To prepare probes to screen the filters containing the cDNA, about 100 ng of single strand cDNA of each type (control and DG-activated) was radiolabelled by adding it to a mixture containing about 12 ul of random primers (Boehringer; about 90 $A_{260}$ U/ml), about 2 MCi $^{32}$p-dCTP (3,000 Ci/mmole; Amersham, Arlington Heights, Ill.), about 0.6 mM each of DATP, dTTP, and dGTP and 40 ul Klenow (Boehringer; about 2 U/ul) in 800 ul of the buffer used for second strand cDNA synthesis (see above). Incubation was conducted overnight at room temperature in 2 400 μl aliquots. This reaction resulted in probes of about $1.2 \times 10^9$ cpm.

After at least 6 hours of prehybridization at about 42° C. in hybridization buffer (see below), the cDNA blots were hybridized to probes. One blot was hybridized to activated DG probes, and a duplicate blot was hybridized to control (normal DG cDNA) probes. The hybridizations were performed in a solution containing 50% formamide, 5× SSCPE (Sambrook et al, 1989), 10× Denhardt's, 0.5% SDS, 0.5 mg/ml herring sperm carrier DNA and the cDNA probe at a concentration of about $1 \times 10^8$ cpm/ml. The blots were incubated for about 48 hours in a shaking 42° C. water bath. After incubation, the blots were washed with 0.1× SSC, 0.2% SDS, 3 times for 1 hour each at 68° C. After exposure to film, those cDNA clones hybridizing stronger to the activated DG probes than the control probes were selected and re-screened using a second set of activated DG and control probes prepared as described above. Those clones that hybridized more strongly to the activated DG probe than to the control probe in two separate screens were sequenced from both ends (about 200–300 bp in from each end) using standard sequencing methods, and these sequences were searched by FASTA analysis (Pearson et al., *Proc. Natl. Acad. Sci. USA*, 85, 2444–2448 [1988]) in GenBank and other public DNA databases. Based on sequence comparison, several clones appeared to be novel. The clones that relate to the present invention were designated as follows: #784, #1441, #2090; #2268; #2282; #7547; #8032; #6734; and #7761.

To obtain full length cDNA clones, a second cDNA library was constructed from activated DG RNA using methods similar to those described above. The library was made as described above using activated DG poly A RNA and oligo-(dT) -XbaI primers (Promega), but only cDNAs larger than 1.5 kb were selected as inserts. This library was plated at high density and transferred to nylon filters (S&S, Keene, N.H.). A probe was generated from the about 0.5 kbp XbaI insert of clone #1441 by isolating this XbaI restricted fragment using the Qiagen Purification Kit (Qiagen, Chatsworth, Calif.) and following the manufacturers recommendations. The fragment was then radioactively labelled with α-$^{32}$P-dCTP using standard methods (RediVue; Amersham, Arlington Heights, Ill.). The filters were hybridized using conditions as described above. Several positive clones were identified from this screening. Two of the positive clones, 1441–10 and 1441–13, were selected as they had the longest inserts (about 1.6 kbp and 1.4 kbp, respectively). These two clones were subjected to DNA sequence analysis on both strands using the dideoxy chain termination method with fluorescent dideoxynucleotides (Applied Biosystems Inc., Foster City, Calif.). The nucleotide sequence was analyzed using Genetics Computer Group software (Univeristy of Wisconsin, Biotechnology Center, Madison, Wis.).

Clone #1441–10 was found to have an insert of about 1604 bp, and harbors a long open reading frame (ORF) encoding a 142 amino acid protein. The full length cDNA of this clone obtained from rat tissue, termed Neuritin, is set forth in FIG. 1 (SEQ ID NO:1). The amino acid sequence of rat Neuritin is set forth in FIG. 3 (SEQ ID NO:3).

Human Neuritin cDNA was cloned using the polymerase chain reaction (Pwo DNA Polymerase and buffer; Boehringer Manheim) under standard conditions which were as follows: 5 minutes denaturation at 94° C. followed by 30 cycles of: 30 seconds at 94° C., 30 seconds at 56° C., and 30 seconds at 72° C. using the following oligonucleotides:
CTAGTCTAGAACCATGGGACTTAAG (SEQ ID NO: 5)
GGTATAGTCGACCCGTGCTCAGAA (SEQ ID NO: 6)
The template for this PCR reaction was double stranded cDNA which was generated from about 2 ug of human cortical mRNA (Clontech, Palo Alto, Calif.) using a Marathon cDNA Amplification Kit (Clontech, Palo Alto, Calif.) following the manufacturers recommendations. Amplified products of the predicted size (about 435 bp) were subcloned into the pCR-Script Amp SK(+) cloning vector (Stratagene, La Jolla, Calif.) and both strands were sequenced using standard sequencing methods. The human Neuritin cDNA sequence is shown in FIG. 2 (SEQ ID NO:2). The predicted amino acid sequence of human Neuritin, based on translation of the cDNA sequence, is set forth in FIG. 4 (SEQ ID NO:4).

Analysis of rat and human Neuritin protein reveals an amino-terminal hydrophobic putative signal peptide of approximately 24 amino acids. The C-terminal 27 amino acid tail is enriched in hydrophobic residues and contains a consensus cleavage signal typically found in GPI (glycosyl phosphotidyl inositol) membrane anchored proteins. The mature, membrane bound protein of 91 amino acids (about 12 kiloDaltons) and 6 cysteine residues. However, this amino acid sequence does not contain general sequence or even motif homology with any known protein as assessed by sequence searching in the public DNA and protein databases (SWISS-PROT, PROSITE, GENBANK, and PIR), suggesting it represents a novel class or family of molecules.

Example II
Preparation of Neuritin Protein and Antibodies

A rat Neuritin cDNA encoding amino acids 30 to 113 of Neuritin ("Neuritin 30–113") was subcloned into the heat inducible bacterial expression vector pCFM1656 (ATCC accession number 69576) for amplification and expression of Neuritin 30–113. Inclusion bodies containing the Neuritin 30–113 were isolated by lysing bacteria in 3 ml of lysis buffer (50 mM Tris, pH 8.0, 1 mM EDTA, and 100 mM NaCl containing 10 mg lysozyme and 10 mg Na-deoxycholate) per gram of bacteria. Lysed bacteria were treated with 400 µg DNase I for 30 min. to 1 hour and then centrifuged at about 12000×g for 15 minutes at about 4° C. Pelleted inclusion bodies were washed 2–4 times in 9 volumes of lysis buffer containing 0.5% NP-40. Purity of Neuritin 30–113 in the inclusion bodies was assessed by SDS-PAGE. Purified inclusion bodies were solubilized (1:20) in 8M urea, 50 mM Tris pH 8.0, 50 mM NaCl and 5 mM dithiothreitol (DTT) for 1–2 hours at room temperature (RT). Non-soluble material was removed by centrifugation at about 14 kg for 10 minutes at RT. Urea was slowly dialyzed against 1 L of the buffer described above using the following time course and concentrations of urea (all dialysis was done at 4° C.): 8M to 6M urea, 1 hour; 6M to 4M, overnight; 4M to 2M, 1 hours; 2M to 1M, 1 hour; 1M to 0.5M, 1 hour; 0.5M to 0.25M, 1 hour, 0.25M to 0M, 1 hour. Refolded Neuritin 30–113 was analyzed on non-reducing SDS-PAGE gels.

To prepare antibodies to Neuritin, the Neuritin peptide fragment:
DCQEGAKDMWDKLRK (SEQ ID NO: 7)
comprising an internal region of mature Neuritin protein was synthesized by standard methods and used for immunization of rabbits (prepared by Berkeley Antibody Company, Berkeley, Calif.) resulting in production of polyclonal antiserum termed AS419. A second polyclonal rabbit antiserum (termed AMG20) prepared against the bacterial expressed Neuritin 30–113 fragment purified from solubilized inclusion bodies as described above was also prepared (Cocalico Biologicals Inc., Reamstown, Pa.). Antisera that specifically reacted in Western blot analyses of recombinant Neuritin prepared in CHO cells was affinity purified using sepharose beads containing the appropriate immobilized Neuritin peptide (Pierce Chemicals, Rockford, Ill.) followed by a protein A/G column (Pierce Chemicals) to concentrate the antibody preparation.

Rat and human recombinant Neuritin spanning amino acids 1–115 was expressed in Chinese hamster ovary cells (CHO cells; ATCC accession number CRL-9096) by transfecting the cells with the plasmid PGREG containing either rat or human Neuritin cDNA. pGREG was prepared from the mammalian expression vector pDSRa2 (described in PCT patent application number WO 90/14363, published 29 Nov. 1990).

pGREG contains, from 5' to 3', a sequence encoding an XhoI restriction enzyme site, a thrombin cleavage site (see SEQ ID NO:8), a herpes simplex virus epitope recognized by Novagen's (Madison, Wis.) monoclonal antibody, (see SEQ ID NO:9), a hexa-histidine epitope for metal-chelate chromatography, a stop codon, and a SalI restriction enzyme site.
LVPRGS (SEQ ID NO:8)
QPELAPEDPEDVE (SEQ ID NO:9)
The HSV/His tag was incorporated into pDSRα2 by staggered PCR using 4 overlapping oligonucleotides at the 3' end of Neuritin and the 5' oligonucleotide described above (SEQ ID NO:5). As template for the PCR, p1441-10 was used. An initial oligonucleotide specific to the 3' end of rat Neuritin coding region incorporated the XhoI and thrombin cleavage site. Three successive PCR reactions progressively incorporated the tagged sequence to the c-terminal end of rat Neuritin. The resulting product was subcloned in to the XbaI and SalI sites of pDSRα2. Additional tagged constructs were generated using PCR products that contained XbaI and XhoI restriction sites.

The human cDNA encoding amino acids 1 to 115 (and lacking the carboxy-terminal GPI-signal peptide) was used to express secreted human Neuritin containing the thrombin cleavage site, herpes simplex virus (HSV) and hexa-Histidine (HIS) epitopes at its C-terminus. Human Neuritin cDNA lacking the GPI-signal peptide (i.e., encoding amino acids 1–115) was generated by PCR using standard conditions and the following oligonucleotides:
CTAGTCTAGAACCATGGGACTTAAG (SEQ ID NO:10)
GGTATACTCGAGCCCGTTGCCGCT (SEQ ID NO:11)
The resulting 373 bp product was subcloned into the XbaI and XhoI sites of PGREG. The resulting vector is named pDSRαhv15Tag.1. The hexa-histidine tag allowed for easy purification of Neuritin on nickel ($Ni^{2+}$) containing resin (Qiagen Inc., Chatsworth, Calif.).

CHO/Neuritin conditioned media was prepared as follows. Roller bottles containing CHO cells stably expressing the human tagged version of Neuritin 1–115 (named hu15t36) were incubated to approximately 80 percent confluence (about 48 hours) in serum free Dulbecco's Minimum Essential Media (DMEM). The conditioned media was harvested by pelleting out cellular debris by centrifugation at about 2500g; the supernatant was stored at −20° C. Neuritin was purified in batch by incubating 1 ml of PBS equilibrated $Ni^{2+}$/NTA resin/100 ml of conditioned media ($Ni^{2+}$/NTA resin supplier: Qiagen Inc., Chatsworth, Calif.). Non-specific proteins were removed by washing the resin with wash buffer (20 mM Na-Phosphate, pH 6.0, and 500 mM NaCl) containing increasing amounts of imidazole (20, 40, 80, and 100 mM). Specifically bound HSV-HIS tagged Neuritin was eluted with 500 mM imidazole. The purified protein (greater than 95 percent pure by silver stain SDS-PAGE [BioRad Laboratories, Hercules, Calif.]) was concentrated about 10-fold and diafiltered (Millipore Corp., [Ultrafree 15, 5K mw cutoff] Bedford, Mass.) into 1× PBS. The final concentration of protein was estimated at 30–50 ng/ml using the Bio-Rad/Lowry protein assay with bovine serum albumin as a standard.

Example III
Tissue Expression of Neuritin
A. Northern Blot Analysis
To assess the expression pattern of Neuritin, a Northern blot containing RNA of various rat tissues including heart, brain, spleen, lung, liver, muscle, kidney, and testis was purchased from Clonetech (Palo Alto, Calif.) and were probed with $^{32}P$-labeled cRNA probes. The cRNA probes were generated from rat Neuritin cDNA subcloned into pBluescript (Stratagene, La Jolla, Calif.) as follows. An approximately 430 bp fragment of the Neuritin clone 1441–10 was obtained by digesting the clone with PvuII and SmaI. This fragment was subcloned into the plasmid pBluescript SK+ (Stratagene, La Jolla, Calif.) which was then named cpg15subclone#2. To generate antisense RNA probe, the plasmid was linearized with BamHi, after which in vitro transcription was conducted using T7 polymerase (Promega, Madison, Wis.) and 32p-UTP. isolated essentially as described above using about 1 ml of guanidinium isothiocyanate lysis buffer.

The quantity of RNA on each blot was assessed by monitoring ethidium bromide staining of size separated RNA and confirmed by hybridization of blots with a random primed labeled cDNA fragment of glyceraldehyde-3-phosphate dehydrogenase (GAPDH).

Northern (RNA) analysis as shown in FIG. 5A identified a single MRNA band of about 1.6 kilo bases expressed in rat brain; a band of much lower intensity was observed in lung tissue, and there was little or no hybridization to mRNA from other tissues.

Figure 5B:
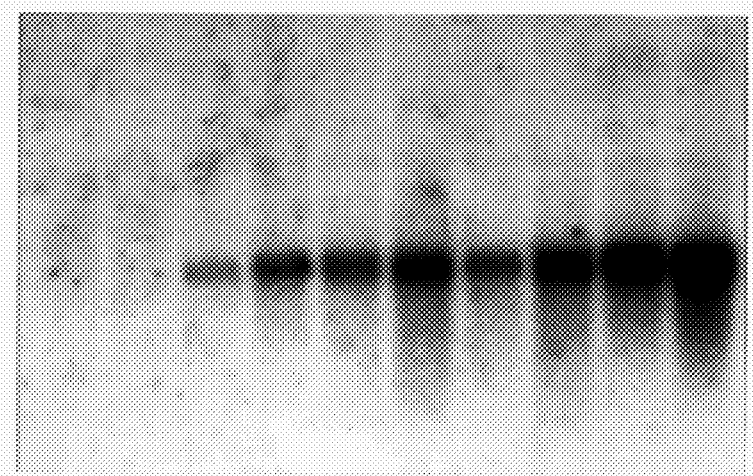
FIG. 5B is a Northern blot of various regions of the brain of either control (−) rats or kainic acid treated (+) rats. Abbreviations are Cereb (cerebellum); Hipp (hippocampus); DG (dentate gyrus). The blot was probed with a Neuritin probe.

To assess expression of Neuritin in various regions of the brain, adult rats were injected intra peritoneally with about 8 mg/kg of a stock solution of 10 mg/ml of kainic acid in PBS. After about six hours, the rats were sacrificed and the brain tissue was dissected. RNA was isolated from various regions of the brain using about 1 ml of guanidinium isothiocyanate lysis buffer (Chomczynski et al., *Anal. Biochem.*, 162:156 [1987]) per 100 mg of pulverized tissue. After lysis, the solution was passed over silica-gel membrane columns (RNeasy spin columns, Qiagen, Chatsworth, Calif.). The RNA was size fractionated by separation on 0.8–1 percent formaldehyde agarose gels and capillary blotted to nylon membranes (Hybond-N, Amersham, Arlington Heights, Ill.). The Northern blots were probed with $^{32}$p-labeled cRNA probes as described above. As can be seen in FIG. 5B, the dentate gyrus region of the brain had the highest level of Neuritin expression.

B. In Situ Hybridization and Immunohistochemistry

In situ hybridization and immunohistochemistry were performed on rat embryo tissue and adult rat brain tissue sections that were paraformaldehyde fixed and paraffin embedded as follows. Embryos from pregnant rats were isolated and fixed overnight in fresh 4% paraformaldehyde in PBS (4% PFA/PBS) at 4° C. before dehydration and paraffin embedding. Adult rat brains were prepared by transcardial perfusion of anesthetized animals with 4% paraformaldehyde in PBS. Dissected brains were then fixed overnight at 4° C. in 4% paraformaldehyde in PBS, dehydrated, and embedded in paraffin. In situ hybridization on these tissue sections was done according to established methods (Simonet, et al, *J. Biol. Chem.*, 11:8221–8229 [1993]) using a rat Neuritin cRNA probe prepared as described above for Northern blots, except $^{35}$S-UTP was used instead of $^{32}$P-UTP. Hybridized slides were exposed to Kodak photographic emulsion and developed after 3–6 weeks after which time the sections were counterstained with hematoxylin, and silver grains were visualized using dark field optics.

Immunohistochemical localization of Neuritin was conducted using varying dilutions of affinity purified antisera (AS419 or AMG20, described above), specific for human recombinant Neuritin prepared in mammalian cells, on deparaffinized PFA fixed tissue sections. Bound Neuritin antibody was detected with biotinylated goat anti-rabbit immunoglobulin and horseradish peroxidase labeled avidin using the Vectastain Elite ABC staining kit (Vector Labs, Burlingame, Calif.) according to the manufacturers instructions.

In situ hybridization analysis showed that Neuritin mRNA is present at the border between the neuroepithelium and the differentiating zone of the developing rat brain as early as embryonic day 14 (E14). The message was also localized in developing neuronal structures in the periphery including the dorsal root ganglia and trigeminal ganglia. Expression appeared to increase throughout development, and it appears to become more concentrated within the differentiating zone as individual structures within the CNS become more defined.

Neuritin mRNA was detected in most structures of the adult brain. The most abundant signals were found in layers II–IV of the cortex, the hippocampal formation, thalamus, habenula, and brainstem. In the hippocampus, expression was concentrated in neurons of the pyramidal and granule cell layer, with abundant levels found in neurons of the subiculum and hilar region of the dentate. In the cerebellum, the low levels of Neuritin message were localized to the granule cell layer with scattered punctate labeling of Purkinje cells.

Immunohistochemical staining of brain tissues using the Neuritin antibodies AS419 or AMG20, described above shows that neuritin is concentrated on neuronal cell bodies and unevenly dispersed along neuritic projections in the non-myelinated regions of the brain. The uneven staining results in a granular appearance of the immunoreactive regions and is particularly evident along the projections of neurons in the subicular complex of the hippocampus. The concentration of neuritin along neurites is also documented in the staining of the dendritic arbors of positive purkinje cells. The hilar region of the DG contains scattered strongly immunoreactive cells that correlate with the pattern observed by in situ hybridization of neuritin mRNA The irregular staining of purkinje neurons also correlates with the punctate message localization.

Example IV

Neuritin Biochemistry and Regulation of Expression

Figure 8A:
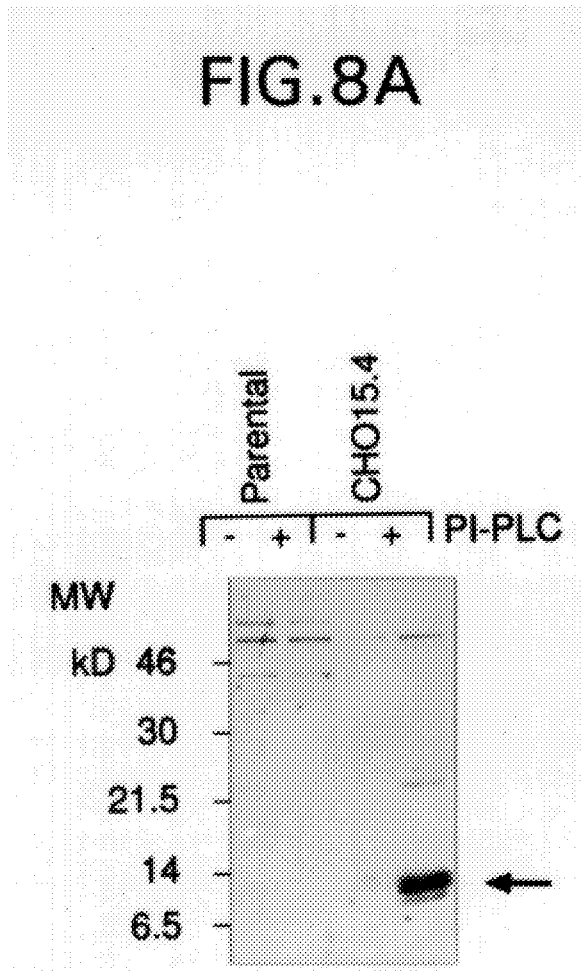
FIGS. 8A and B depict two Western blots probed with an antibody against Neuritin.

The amino acid sequence of the carboxy terminus of Neuritin suggested the possibility that Neuritin is membrane anchored. To evaluate this possibility, about $1 \times 10^6$ CHO cells transfected with either an empty plasmid (termed "parental" and containing no Neuritin gene) or with a plasmid containing the gene encoding human Neuritin were treated with either about 0.4 U/ml of PI-PLC (phosphatidyl inositol-phospholipase C; Calbiochem, La Jolla, Calif.) prepared in 0.5 ml release buffer (25 mM Tris-HCl, pH 7.5, 1 mM EDTA, 10 mM Glucose, 250 mM sucrose), or with release buffer alone (no PI-PLC) following published methods (Kodukula et al., *J. Cell Biol.* 120:657 [1993]). After incubation, the cells were centrifuged to precipitate cellular debris. The supernatants were analyzed by SDS-polyacrylamide gel electrophoresis (SDS-PAGE). After electrophoresis, the gels were blotted on to nitrocellulose paper and probed with Neuritin specific affinity purified antisera. The results are shown in FIG. 8A. As can be seen, all detectable Neuritin was found in the supernatants of the CHO cells expressing Neuritin that had been treated with PI-PLC, suggesting that Neuritin is indeed GPI anchored.

Figure 8B:
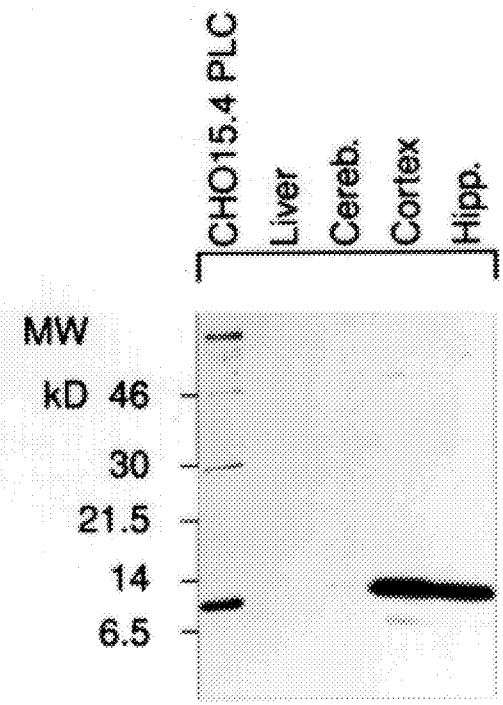
FIG. 8B depicts a Western blot of various tissues from rats. The blot was probed with a Neuritin antibody. Abbreviations for the tissues evaluated in this blot are found in the text.
Figure 9A:
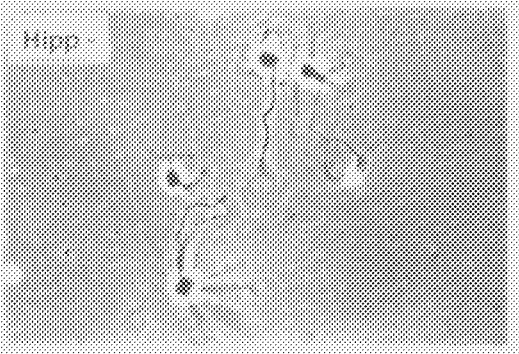
FIG. 9 depicts cultures of hippocampal ("Hipp") and cortical ("Cort") rat embryonic neurons incubated in the presence (+) or absence (−) of Neuritin. "DiI" refers to treatment with the lipophilic fluorescent dye DiI.
Figure 9B:
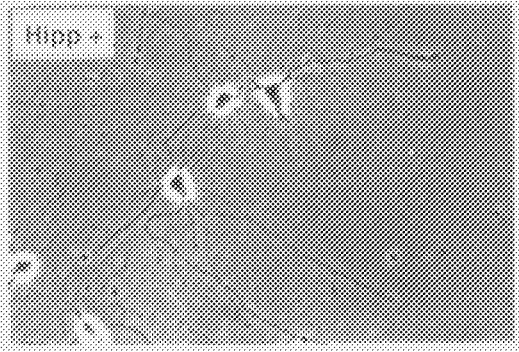
Figure 9C:
Figure 9D:
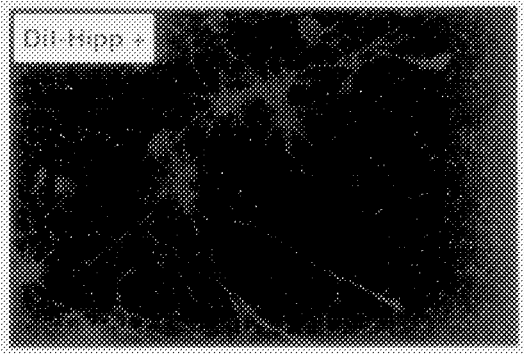
Figure 9E:
Figure 9F:

Analysis of this endogenous GPI-anchored Neuritin was done by extracting tissue with the detergent Triton X-114 (Calbiochem, San Diego, Calif.) according to the method described by Borchelt et al. (*Glycobiol.* 3:319 [1993]) to obtain native Neuritin. Approximately 100 mg of pulverized tissue was suspended in 0.5 ml of 1× TNE buffer (50 mM Tris-HCl, pH 7.5, 150 mM NaCl, 5 mM EDTA) with protease inhibitors (0.5 mM benzamidine, 1 mM PMSF, and 1 μg/ml each of pepstatin, leupeptin, aprotinin) and mixed at 4° C. with about 0.25 volumes of Triton X-114 pre-equilibrated with 1× TNE. The Triton X-114 soluble proteins were extracted from solution by incubating the mixture at 30° C. for about 15 minutes followed by centrifugation at about 3000 g for 5 minutes at room temperature to precipitate the large, lipophilic-protein containing detergent micelles. This extraction was repeated and the detergent-containing soluble fractions were pooled. To analyze the extracted proteins by Western blot, 20–40 μl aliquots of the detergent fractions were precipitated by incubating each aliqout with 10 volumes of methanol (10 minutes at 4° C. followed by spinning at 14,000 g for 15 minutes at 4° C.). The precipitated pellet was resuspended in about 40 ul of SDS-PAGE sample buffer (containing beta-mercaptoethanol), and size fractionated on a 16 percent SDS-PAGE gel (Novex, San Diego, Calif.). After electrophoresis, the proteins were transferred on to nitrocellulose paper using standard Western blotting procedures. Neuritin was detected using Neuritin-specific affinity-purified antisera (AS419 or AMG20, described above) as a first antibody, and horse radish peroxidase conjugated goat-anti-rabbit antisera as a second antibody (diluted about 1:10$^4$, obtained from Southern Biotechnology Associates, Inc., Birmingham, Alabama). Antibody was detected using peroxidase sensitive enhanced chemiluminescence ("ECL", Amersham, Arlington Heights, Ill.). The results are shown in FIG. 8B. As is apparent, the cortex and hippocampus regions of the brain expressed the highest levels of Neuritin. Neuritin from recombinant CHO cells, prepared as described above using PI-PLC is shown in lane 1 as a comparison. The difference in the migration of Neuritin in the lanes on the Western blot is presumably due to the altered mobility of Neuritin to which some lipid is attached.

Figure 6A:
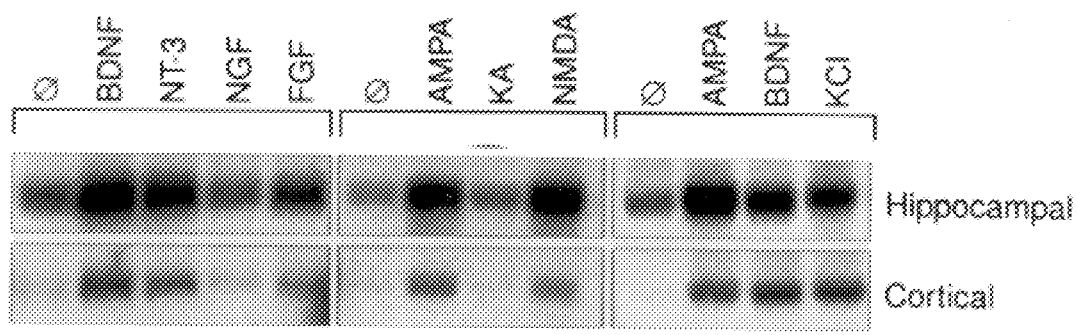
FIGS. 6A and B depict various Northern blots.

To investigate the regulation of Neuritin MRNA expression, recombinant human BDNF, NT-3, NGF, or FGF (about 10 ng/ml), KCl (about 50 mM), or the calcium channel blockers AMPA or NMDA (about 10 μM) was added to 7DIV E18 rat hippocampal or cortical cultures prepared as described below in Example V. RNA was isolated from each culture after about six hours of incubation by the RNeasy method (Qiagen, Chatsworth, Calif.). About 5 μg of this RNA was loaded on to a gel, separated by electrophoresis, and then Northern blotted. The blot was probed with a rat Neuritin cRNA probe spanning the coding region (described above). The results are shown in FIG. 6A. As can be seen, NMDA and AMPA treatment resulted in an approximately 5-fold increase in Neuritin mRNA levels, and a similar magnitude of induction was observed with depolarizing concentrations of KCl.

Figure 6B:
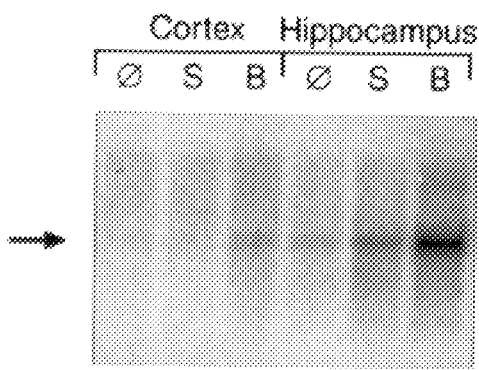
FIG. 6B shows a Northern blot of hippocampal and cortex RNA obtained from rats injected with saline ("S") or BDNF ("B"). "0" indicates no treatment.

To evaluate the effect of BDNF on Neuritin expression levels in vivo, BDNF (1–2 μl of 10 mg/ml) or saline (control) was intraventricularly injected into postnatal day 4 rat pups. About six hours after administration of BDNF or saline, the pups were sacrificed and total RNA was isolated from cortex or hippocampal brain tissue. As can be seen in FIG. 6B, BDNF induced Neuritin message in vivo primarily in the hippocampus, and to a small degree in the cortex.

Example V

Neuritin Bioactivity Assays

Cultures of primary hippocampal and cortical embryonic rat neurons were prepared by dissociating dissected brain regions from embryonic day 18 rat embryos. Dissociation and purification of embryonic neurons was conducted using a papain-based tissue dissociation kit (Worthington Biochemical Corp., Freehold, N.J.). Dissected tissue from 10–30 embryos was resuspended in 2.5 ml Earles balanced salt solution (EBSS) containing: 50 units papain, 1 mM L-cysteine, with 0.5 mM EDTA and 500 units DNase I). Tissue was dissociated for 10–15 minutes with gentle shaking. Dissociated cells were pelleted at 300 g for 5 minutes, resuspended in 2.7 ml EBSS, 0.3 ml ovomucoid inhibitor solution (10 mg/ml ovomucoid protease inhibitor and 10 mg/ml bovine serum albumin) and 250 units DNase I. The suspension was overlayed onto 5 ml of ovomucoid inhibitor solution and pelleted at 70 g for 6 minutes. Pelleted cells were resuspended in 10 ml of B27 containing Neurobasal media (Gibco/BRL, Grand Island, N.Y.) and passed through a 40 μm nylon mesh cell strainer (Becton Dickinson, Lincoln Park, N.J.). For RNA analysis, the dissociated neurons were plated on 6-well Falcon tissue culture plates (Becton Dickinson, Lincoln Park, N.J.) pre-coated with poly-L-ornithine (obtained from Sigma, St. Louis, Mo., and used at a concentration of about 0.1 mg/ml in 150 mM Na-Borate, pH 8.4) and laminin (obtained from Gibco/BRL, Grand Island, N.Y., and used at about a concentration of 1 μg/ml in PBS). Plating of the neurons was at a density of about 2×10$^5$ per cm$^2$ for hippocampal neurons and about 3×10$^5$ per cm$^2$ for cortical neurons. The cells were grown in Neurobasal media (Gibco/BRL, Grand Island, N.Y.) supplemented with 1× B-27 supplement (Gibco/BRL, Grand Island, N.Y.) and 50 mg/ml gentamycin sulfate (Gibco/BRL, Grand Island, N.Y.) Glial cell content of each culture after seven days of culture was less than five percent as assessed by counting glial fibrillary acidic protein (GFAP) positive cells which were identified by indirect immunofluoresence staining using antibody specific to this glial cell specific marker. Cells were treated as described after 7 to 8 days of culture.

The neurite outgrowth assay was conducted using hippocampal and cortical neurons prepared as above. The cells were plated on poly-lysine (20 μg/ml in PBS) coated 35 mm plates at a density of about 5×10$^3$ cells per cm$^2$ in the presence or absence of Ni$^{2+}$ purified Neuritin (prepared as described above). Neurite outgrowth was assessed after four days of culture by staining the live cultures with the non-specific lipophilic dye, DiI (10 uM, visualized with 565 nm filter), for about 30 minutes at 37° C., followed by 3 washes in B-27 supplemented neurobasal media (see above) prior to analysis.

To examine the biological function of Neuritin, a histidine tagged version of Neuritin lacking the carboxyl terminal 27 amino acids was produced in Chinese hamster ovary (CHO) cells and purified from serum free conditioned media by Ni2+ affinity chromatography to more than ninety percent homogeneity, as determined by silver staining of SDS-polyacrylamide gels (see above). Hippocampal and cortical neurons from E18 rat embryos were plated on poly-lysine coated dishes in the presence of about 150 ng/ml of this recombinant Neuritin. The same volume was added to the controls using an equivalent Ni2+ affinity fraction derived from conditioned media from CHO cells transfected with the empty expression vector. After four days in culture, the neurons plated in the presence of neuritin showed extensive neuritogenesis over the control cultures, as is shown in FIG. 9. Neuritin treated cells had longer, more highly branched neurite arbors and an increased number of neurites extending from the soma as compared to control cells. Cells that were nonspecifically stained with the lipophilic fluorescent dye, DiI, revealed a striking difference in the organization of the soma and neurite lamellapodia (FIG. 9). Untreated control cells had flat cell bodies and broad, apparently unfocused, lamellapodia along the length or toward the end of many neurites, whereas Neuritin treated cells had well differentiated cell bodies with thin, well-defined extensions. Similar neuritogenic activity was observed with purified bacterial Neuritin.

Deposit of Neuritin cDNA

The cDNA encoding full length human Neuritin has been deposited with the ATCC (American Type Culture Collection, 12301 Parklawn Drive, Rockville, Md., USA) on Aug. 09, 1996 as accession number 98134.

---

We claim:

1. An isolated neuritin polypeptide which promotes neuritogenesis in hippocampal or cortical neuronal cultures wherein said polypeptide is selected from the group consisting of:
   (a) a polypeptide having the amino acid sequence of SEQ ID NO:3;
   (b) a polypeptide having the amino acid sequence SEQ ID NO:4;
   (c) a polypeptide that is at least 70 percent identical to the polypeptide of (a) or (b) as determined by FASTA or BLAST using default opening and gap penalties and a PAM 250 scoring matrix.

2. An isolated neuritin polypeptide which promotes neuritogenesis in hippocampal or cortical neuronal cultures wherein said polypeptide has the amino acid sequence of SEQ ID NO:3 or a biologically active fragment thereof.

3. An isolated neuritin polypeptide which promotes neuritogenesis in hippocampal or cortical neuronal cultures wherein said polypeptide has the amino acid sequence of SEQ ID NO:4 or a biologically active fragment thereof.

4. The neuritin polypeptide of claim 3 that does not possess an amino terminal methionine.

5. The neuritin polypeptide of claim 4 selected from the group consisting of: amino acids 25–115 of SEQ ID NO:4, amino acids 1–115 of SEQ ID NO:4, amino acids 1–113 of SEQ ID NO:4.

* * * * *

UNITED STATES PATENT AND TRADEMARK OFFICE
CERTIFICATE OF CORRECTION

PATENT NO.   : 5,859,197
DATED        : January 12, 1999
INVENTOR(S)  : THEILL, et al.

It is certified that error appears in the above-identified patent and that said Letters Patent is hereby corrected as shown below:

Column 11, line 52:  Change "typically no" to --this way will--.

Column 20, line 10:  Change "$H_{20}$" to --$H_2O$--.

Column 23, line 63:  Change "PGREG" to --pGREG--.

Column 24, line 32:  Change "PGREG" to --pGREG--.

Column 25, line 10:  Change "32p-UTP" to --$^{32}$p-UTP--.

Column 25, line 19:  Change "MRNA" to --mRNA--.

Column 27, line 37:  Change "MRNA" to --mRNA--.

Signed and Sealed this

Twenty-sixth Day of October, 1999

Q. TODD DICKINSON

*Attest:*

*Attesting Officer*    *Acting Commissioner of Patents and Trademarks*